US010512541B2

(12) United States Patent
Zerkowski et al.

(10) Patent No.: US 10,512,541 B2
(45) Date of Patent: Dec. 24, 2019

(54) MEDICAL DEVICE FOR A CARDIAC VALVE IMPLANT

(71) Applicant: MEDTENTIA INTERNATIONAL LTD OY, Espoo (FI)

(72) Inventors: Hans-Reinhard Zerkowski, Reihen (CH); Ger O'Carroll, Castlebaldwin (IE); Mark Pugh, Coolaney (IE)

(73) Assignee: Medtentia International Ltd. Oy, Espoo (FI)

( * ) Notice: Subject to any disclaimer, the term of this patent is extended or adjusted under 35 U.S.C. 154(b) by 334 days.

(21) Appl. No.: 15/119,267

(22) PCT Filed: Feb. 18, 2015

(86) PCT No.: PCT/EP2015/053420
§ 371 (c)(1),
(2) Date: Aug. 16, 2016

(87) PCT Pub. No.: WO2015/124631
PCT Pub. Date: Aug. 27, 2015

(65) Prior Publication Data
US 2017/0007402 A1 Jan. 12, 2017

(30) Foreign Application Priority Data
Feb. 18, 2014 (EP) .................................. 14155508

(51) Int. Cl.
A61F 2/24 (2006.01)
(52) U.S. Cl.
CPC .......... A61F 2/2445 (2013.01); A61F 2/2466 (2013.01); A61F 2230/0091 (2013.01)

(58) Field of Classification Search
CPC ...... A61F 2/2427; A61F 2/243; A61F 2/2433; A61F 2/2436; A61F 2/2439; A61F 2/2466; A61F 2/95; A61F 2/954; A61F 2/962; A61F 2/966; A61F 2002/2484; A61F 2002/9505; A61F 2002/9511;
(Continued)

(56) References Cited

U.S. PATENT DOCUMENTS 5,109,867 A * 5/1992 Twyford, Jr. ..... A61M 25/0905
403/223
5,217,484 A * 6/1993 Marks .............. A61B 17/12022
128/899

(Continued)

Primary Examiner — Ryan J. Severson
(74) Attorney, Agent, or Firm — Patent Grove LLC; Tomas Friend

(57) ABSTRACT

A medical device for delivering and retrieving a medical implant is disclosed comprising a sheath, a wire having a distal end and being movable in a lumen of the sheath in a longitudinal direction of the sheath. The distal end comprises a locking structure for receiving and interlock with a complementary mating surface of a medical implant, wherein the locking structure comprises a first locking surface aligned in a first radial direction to lock rotational movement of the implant, when received in the locking structure, around the longitudinal direction. The wire comprises a pivotable locking portion having an open and a closed position, the locking portion has a locking structure with a recess locking movement of the implant, when received in the locking structure, in the longitudinal direction, when the locking portion is in the closed position.

26 Claims, 8 Drawing Sheets

(58) Field of Classification Search
CPC ...... A61F 2002/9517; A61F 2002/9528; A61F 2002/9534; A61F 2002/9665
See application file for complete search history.

(56) References Cited

U.S. PATENT DOCUMENTS

| | | | | |
|---|---|---|---|---|
| 5,250,071 A * | 10/1993 | Palermo | ............... | A45D 42/24 128/898 |
| 5,261,916 A * | 11/1993 | Engelson | ......... | A61B 17/12022 604/171 |
| 5,853,375 A * | 12/1998 | Orr | ................ | A61M 25/0905 600/585 |
| 5,895,391 A * | 4/1999 | Farnholtz | ......... | A61B 17/12022 606/108 |
| 5,925,059 A * | 7/1999 | Palermo | ........... | A61B 17/12022 606/191 |
| RE37,117 E * | 3/2001 | Palermo | ........... | A61B 17/12022 128/898 |
| 6,296,622 B1 * | 10/2001 | Kurz | ............... | A61B 17/12022 604/93.01 |
| 6,623,518 B2 * | 9/2003 | Thompson | ............... | A61F 2/91 606/108 |
| 6,849,081 B2 * | 2/2005 | Sepetka | ........... | A61B 17/12022 606/1 |
| 6,911,016 B2 * | 6/2005 | Balzum | ............. | A61M 25/0905 600/585 |
| 7,344,553 B2 * | 3/2008 | Opolski | ............. | A61B 17/0057 606/205 |
| 7,473,266 B2 * | 1/2009 | Glaser | ................ | A61B 17/0057 606/200 |
| 8,062,325 B2 * | 11/2011 | Mitelberg | ................. | A61F 2/95 606/200 |
| 8,216,302 B2 * | 7/2012 | Wilson | .................. | A61F 2/2427 623/2.11 |
| 8,506,623 B2 * | 8/2013 | Wilson | .................. | A61F 2/2427 623/2.11 |
| 8,852,270 B2 * | 10/2014 | Maurer | ................. | A61F 2/2442 623/2.11 |
| 9,517,129 B2 * | 12/2016 | Wilson | .................. | A61F 2/2427 |
| 9,770,330 B2 * | 9/2017 | Maurer | ................. | A61F 2/2442 |
| 9,907,555 B2 * | 3/2018 | Buiser | .............. | A61B 17/12022 |
| 9,993,234 B2 * | 6/2018 | Maslanka | .......... | A61B 17/0057 |
| 2002/0120323 A1 * | 8/2002 | Thompson | ................ | A61F 2/91 623/1.11 |
| 2003/0181945 A1 * | 9/2003 | Opolski | ............. | A61B 17/0057 606/206 |
| 2004/0181256 A1 * | 9/2004 | Glaser | ................ | A61B 17/0057 606/213 |
| 2005/0149182 A1 * | 7/2005 | Alferness | .............. | A61F 2/2451 623/2.36 |
| 2007/0299461 A1 * | 12/2007 | Elliott | .............. | A61B 17/12022 606/191 |
| 2009/0043331 A1 * | 2/2009 | Buiser | .............. | A61B 17/12022 606/195 |
| 2009/0132033 A1 * | 5/2009 | Maurer | ................. | A61F 2/2442 623/2.11 |
| 2012/0053687 A1 * | 3/2012 | Migliazza | ............. | A61F 2/2448 623/2.37 |
| 2012/0143301 A1 * | 6/2012 | Maslanka | .......... | A61B 17/0057 623/1.11 |
| 2014/0379075 A1 * | 12/2014 | Maurer | ................. | A61F 2/2442 623/2.11 |
| 2017/0007402 A1 * | 1/2017 | Zerkowski | ............ | A61F 2/2445 |

* cited by examiner

MEDICAL DEVICE FOR A CARDIAC VALVE IMPLANT

FIELD OF THE INVENTION

This invention pertains in general to the field of cardiac valve replacement and repair. More particularly the invention relates to a medical device for delivering and retrieving a catheter deliverable cardiac valve implant, a catheter deliverable cardiac valve implant, and a kit comprising such delivery and retrieval device and implant, such as an annuloplasty ring or helix.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. Such annuloplasty rings or other annuloplasty implants or cardiac valve implants in general such as replacement valves, are put into position by various tools.

WO2012/027500 discloses an annuloplasty ring that is ejected out of a catheter by means of a pusher tool. It is also disclosed that the annuloplasty ring is attached to the delivery system by a wire that can be pulled to direct the tip of the implant.

A problem with prior art delivery devices is lack of steerability or maneuverability of the implant, thereby increasing the amount of manipulation of the implant both during the positioning phase and during repositioning to get the implant in the correct position, which may lead to a more complicated and time consuming procedure. During heart surgery, a premium is placed on reducing the amount of time used to replace and repair valves as the heart is frequently arrested and without perfusion.

A problem with prior art devices is also the time consuming attachment or detachment of the annuloplasty device, also referred to as the cardiac valve implant, or simply implant below, to the delivery or retrieval device, e.g. by using sutures. It would therefore be very useful to have a medical device for holding the implant to be positioned that can be quickly attached or detached to such implant. If repositioning of the cardiac valve implant becomes necessary it is also critical that the retrieval device can engage the implant easily and quickly.

A further problem with prior art devices is less-than-optimal engagement mechanisms between the implant and the delivery wire that does not provides sufficient reliability and/or requires exact, i.e. time consuming, navigation and manipulation before final securement is achieved.

The above problems may have dire consequences for the patient and the health care system. Patient risk is increased.

Hence, an improved medical device for delivering and retrieving a cardiac valve implant would be advantageous and in particular allowing for increased maneuverability, reducing the time of lengthy surgery procedures, cost-effectiveness, and increased patient safety. Also, a kit comprising such device and an annuloplasty implant would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a medical implant delivery and retrieval device is provided comprising a sheath, a wire having a distal end and being movable in a lumen of the sheath in a longitudinal direction of the sheath. The distal end comprises a locking structure for receiving and interlock with a complementary mating surface of a medical implant, wherein the locking structure comprises a first locking surface aligned in a first radial direction to lock rotational movement of the implant, when received in the locking structure, around the longitudinal direction. The wire comprises a pivotable locking portion having an open and a closed position, the locking portion has a locking structure with a recess locking movement of the implant, when received in the locking structure, in the longitudinal direction, when the locking portion is in the closed position.

According to a second aspect of the invention a medical implant delivery and retrieval device is provided comprising a sheath, a wire having a distal end and being movable in a lumen of said sheath in a longitudinal direction of said sheath, said distal end comprising a locking structure for receiving and interlock with a complementary mating surface of a medical implant, wherein said locking structure comprises a locking surface aligned in a radial direction to lock movement of said implant, when received in said locking structure, transverse to said longitudinal direction, wherein said locking surface is curved in a radial direction.

According to a third aspect of the invention a kit is provided comprising a medical implant delivery and retrieval device according to the first aspect of the invention, and an annuloplasty implant such as an annuloplasty ring or helix, wherein the annuloplasty implant comprises a complementary mating surface at an end portion thereof for interlocking with a locking structure of the medical implant delivery and retrieval device.

According to a fourth aspect of the invention an annuloplasty implant such as an annuloplasty ring or helix is provided comprising a complementary mating surface at an end portion thereof for interlocking with a locking structure of a medical implant delivery and retrieval device extending along a longitudinal direction. The mating surface comprises a first locking surface aligned in a first radial direction to lock rotational movement of the implant, when received in the locking structure, around the longitudinal direction. The mating surface comprises a recess for locking movement of the implant, when received in the locking structure, in the longitudinal direction.

Further embodiments of the invention are defined in the dependent claims, wherein features for the second and subsequent aspects of the invention are as for the first aspect mutatis mutandis.

Some embodiments of the invention provide for increased steerability or maneuverability of the implant.

Some embodiments of the invention provide for less time consuming positioning of an implant at a target site in the heart.

Some embodiments of the invention provide for less time consuming attachment and detachment of an implant to a medical device for efficient positioning and repositioning of such implant at the annulus.

Some embodiments of the invention provide for increased accuracy in positioning an implant at the annulus and thereby reducing the risk of complications.

Some embodiments of the invention also provide for a reduced risk of damaging the cardiac valve implant during a repair or replacement procedure.

Some embodiments of the invention provide for better ability to retrieve and reposition an implant.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
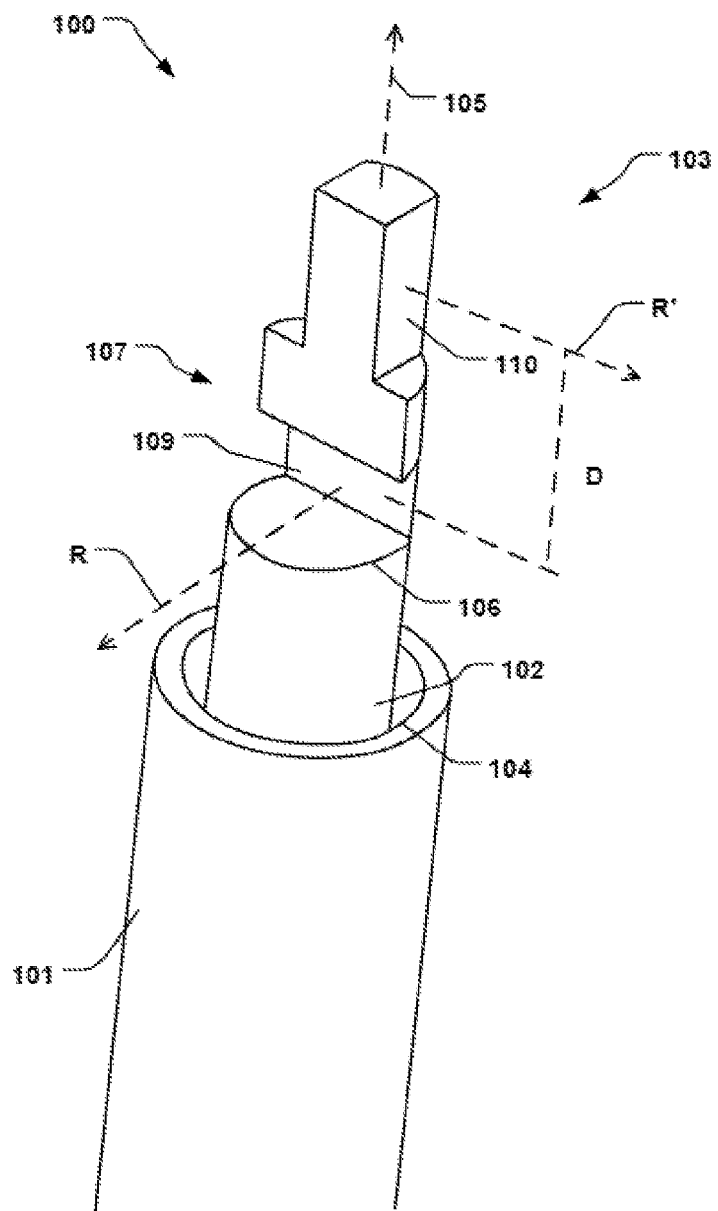
FIG. 1 is an illustration of a medical device according to an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 2A:
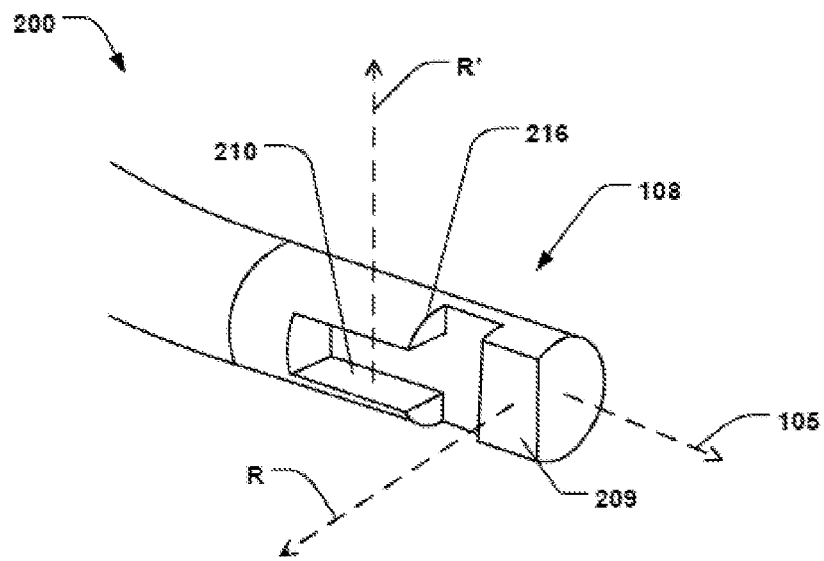
FIGS. 2a-b are illustrations of a cardiac valve implant according to embodiments of the invention, to be positioned with a medical device according in FIG. 1.
Figure 2B:
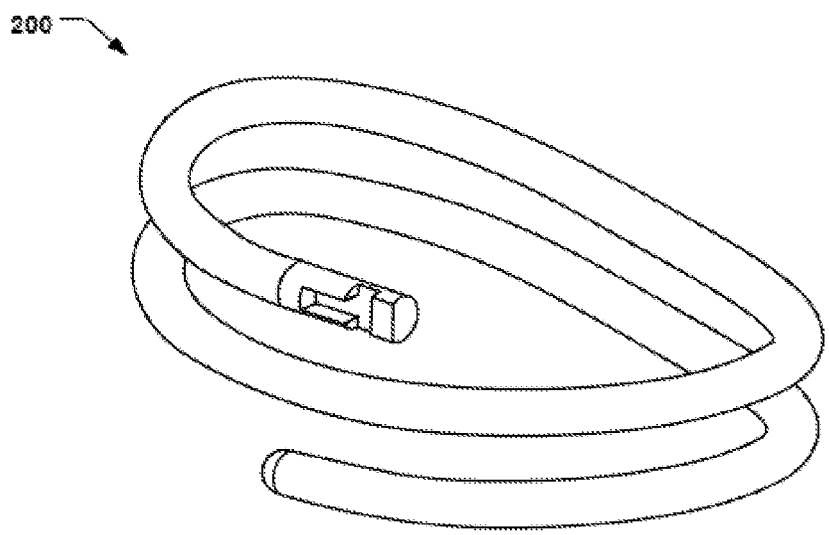

FIG. 1 shows a medical implant delivery and retrieval device 100 comprising a sheath 101, a wire 102 having a distal end 103 and being movable in a lumen 104 of the sheath 101 in a longitudinal direction 105 of the sheath. The distal end 103 comprises a locking structure 107 for receiving and interlock with a complementary mating surface 108 of a medical implant 200, such as shown in FIGS. 2a-b. The locking structure 107 comprises a first locking surface 109 aligned in a first radial direction (R) (indicated by dashed arrow in FIG. 1) to lock rotational movement of the implant 200, when received in the locking structure 107, around the longitudinal direction 105, i.e. around the longitudinal axis 105. The locking structure 107 comprises a second locking surface 110 aligned to face a second radial direction (R'), different from the first radial direction (R), to lock movement of the implant 200, when received in the locking structure 107, transverse to the longitudinal direction 105. The second locking surface 110 thereby prevents movement of an implant 200 in a transverse direction, such as in the second radial direction (R') while the first locking surface 109 hinders the implant from rotating around axis 105. The implant 200 have a complementary mating surface 108 comprising first 209 and second 210 locking surfaces that are positioned opposite, i.e. parallel with, first 109 and second 110 locking surfaces of the device 100. By having two locking surfaces 109, 110, in facing different radial directions, the implant 200 can be effectively held in place by the device 100 without dislocating when handling of the implant. For example, torque can effectively be transmitted from the wire 102 to the implant 200, due to the first locking surface 109, while the implant 200 can be kept securely in the central position relative the longitudinal axis 105, i.e. co-axially positioned relative axis 105 due to the second locking surface 110 fixating the implant 200 in the transverse direction relative longitudinal axis 105, such as in the radial direction. This provides for improved maneuverability of the implant 200 since it is kept in a well-defined secure position relative wire 102 without undesired movement relative the latter. The second locking surface 110 provides for fixating the position in several directions transverse to the longitudinal axis 105, i.e. any transverse direction which has an angle towards the second locking surface 110, i.e. not parallel to the second locking surface 110. The second locking surface 110 provides for secure retrieval of the implant 200 if repositioning or any other adjustments becomes necessary during the procedure, since the position of the implant in the radial direction can be controlled, e.g. in the direction (R') or any other transverse direction with a vector component in a radial direction to the longitudinal axis 105. By securing the position in the radial direction, the implant 200 can be easily withdrawn into sheath 101, for removing the implant or just keeping the implant in the longitudinally locked position as described further below. In this example, if the position of the implant 200 is not secured in a second radial direction, as provided by the second locking surface 110, it will be more difficult or impossible to withdraw the implant 200 into the sheath 101. It should be noted that the first locking surface 109, besides from preventing rotational movement of the implant 200, also stops movement of the implant 200 in a radial direction, different from the (second) radial direction in which the second locking surface 110 stops movement. A radial direction in this disclosure should be construed as directions having any angle of 0-360 degrees around the longitudinal axis 105. For example, if the first locking surface 109 is aligned to face a radial direction (R) of 0 degrees, then the second locking surface may be aligned to have a radial direction (R') of 90 degrees as exemplified in FIG. 1.

Figure 3A:
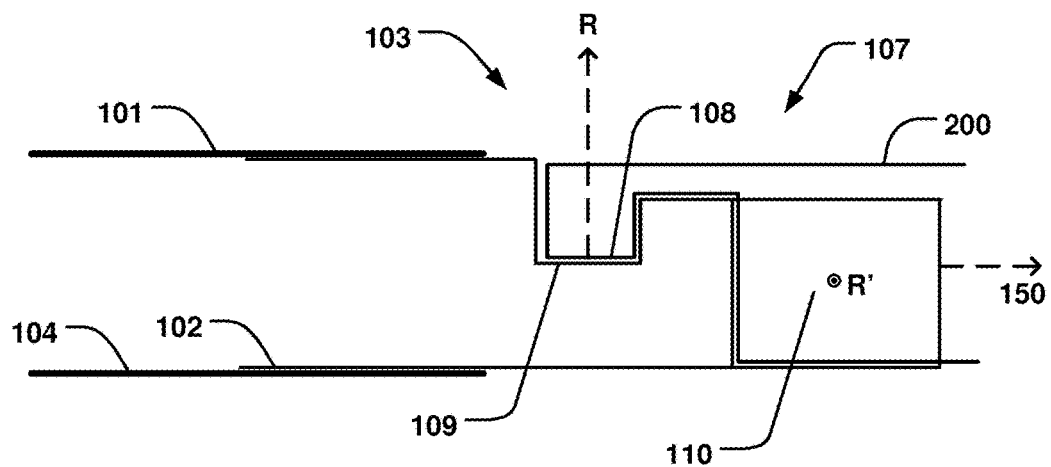
FIGS. 3a-b are illustrations of the cardiac valve implant in FIG. 2 held in place with a medical device in FIG. 1 according to embodiments of the invention.
Figure 3B:
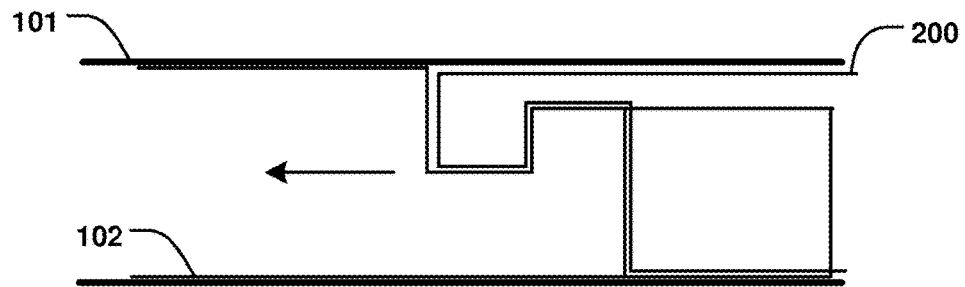

The locking structure 107 may comprise a recess 106 adapted to interlock with the complementary mating surface 108 to lock longitudinal movement of the implant 200, when received in the locking structure 107, along the longitudinal direction 105. FIGS. 3a-b shows a side view of the device 100 when interlocked with the implant 200. Recess 106 mates with a corresponding protrusion of the complementary mating surface 108 to fixate the position along the longitudinal axis 105. This further provides for improving control of the positioning of the implant 200 in the device 100 in order to accurately deliver, manipulate, and possibly retrieve the implant 200 during a procedure. The recess 106 allows the implant 200 to be drawn into the sheath 101. The locking structure 107 may thus be arranged to receive the complementary mating surface 108 when the locking structure extends outside the sheath 101, and to interlock with the complementary surface 108 and fixate the position of the implant 200 relative the locking structure 107 when the locking structure is retracted within the sheath 101. Hence, when in the withdrawn position, the sheath 101 restricts movement of the implant 200 in a radial direction in which the implant was received into the locking structure 107 in the extended position.

Figure 4A:
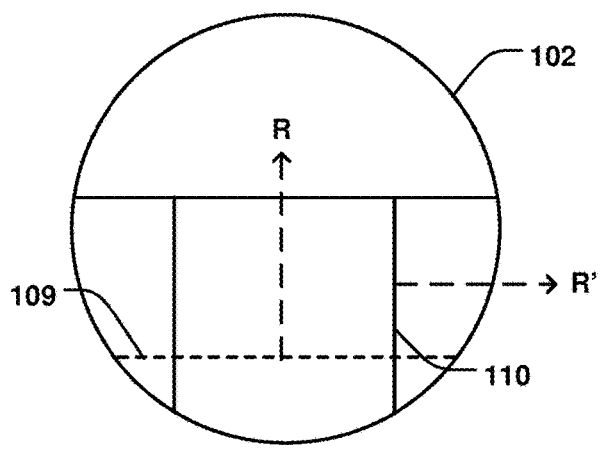
FIGS. 4a-f are illustrations of cross-sectional views from an axial perspective of the medical device in FIGS. 1 and 3 according to an embodiment of the invention.
Figure 4B:
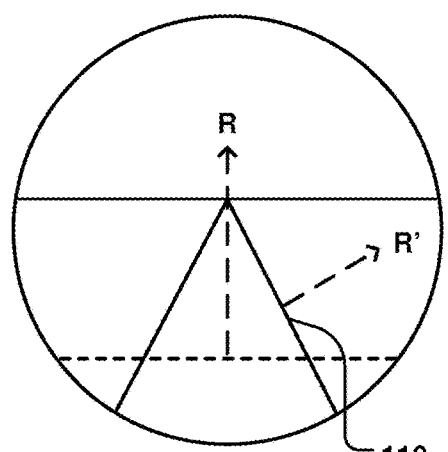

The first (R) and second (R') radial directions may be substantially perpendicular. This may provide for a more optimal locking engagement with the implant 200, as the first and second locking surfaces 109, 110, thereby complements each other in restricting movement in any radial vector component which is not parallel to any of the surfaces. Even if non-perpendicular locking surfaces 109, 110, would also cover all angles of movement, a perpendicular arrangement may make the connection between the locking structure 107 and the complementary mating surface 108 of the implant 200 easier. In FIG. 3a the second radial direction (R') is perpendicular to both the first radial direction (R) and the longitudinal axis 105. The second locking surface 110 may however also form an angle relative the longitudinal axis (not shown), e.g. so that the surface 110 is part of a tapered distal portion of the locking structure 107. If the distal portion is tapered towards the implant 200 it may allow for easier guiding of the implant 200 into the distal portion of the locking structure 107, while at the same time providing for locking transverse movement when interlocked as described above. Alternatively, or in addition, the second radial direction (R') may have any angle relative the first radial direction (R). FIGS. 4a-f shows a cross-sectional view of the distal end 103 i.e. perpendicular to the view in FIGS. 3a-b. The wire 102 has a circular profile in the examples. FIG. 4a illustrates the locking structure in FIGS. 1 and 3a-b, where the first radial direction (R) is perpendicular to the second radial direction (R'). In FIG. 4a the second locking surface 110 is angled towards the first radial direction (R), i.e. forming a distal portion that tapers towards the first radial direction (R). This may provide for easier engagement with the implant 200 since the tapered portion may guide the implant into the final interlocked position along the first radial direction (R).

The locking structure 107 may be open radially outwards to receive the complementary mating surface 108 in a radial direction. As seen in e.g. FIG. 3a, this provides for convenient interlocking with the implant 200 since the implant can be approached from the side and guided radially inwards.

The first and/or said second locking surface 109, 110, may be substantially flat. Hence, while the locking structure 107 provides for controlled fixation of the implant 200 the mating surfaces of the locking structure 107 and the implant 108 have a minimum of connecting portions that must be aligned, that also makes interlocking easier, and particularly of subsequent retrieval of the implant 200 is necessary.

Alternatively, or in addition, the first and/or said second locking surface 109, 110, may be curved or comprise a curved portion. The advantage of having a curved surface is that the implant may be smoothly guided into the correct position, by tracking the curved surface, as described further below. This may be advantageous if retrieval of the implant is required and the surrounding anatomy is moving due to the beating heart. The curved surface allows a certain off-set in relation to the final position of the implant when making first contact with the implant to be retrieved with the wire 102, which is appreciated due to the movement of the implant in relation to the wire, both due to the beating heart and the manipulation of the wire by the surgeon. The curved surface will guide the implant into the final secured positioned by a sliding movement. The curved locking surface is advantageously arranged to receive the entire portion of the implant that is in contact with the distal wire 102 in the final locked position. I.e. avoiding portions of the complementary locking surfaces of the wire and the implant that are not contributing to the guiding of the implant to the final position, will optimize the ability to guide the implant and also to achieve the most secure and stable position once the implant has arrived at the final position. The entire surface of the distal end of the wire that is in contact with the implant may thus be curved. Prior art devices may have curved portions of the wire, but are intended only as an opening through which a neck portion of the implant may pass, i.e. no complementary locking surfaces. Further, the bulk of the implant that is actually in contact with the wire in the final locked position is merely resting on a flat surface that has no ability to guide the implant.

Figure 4C:
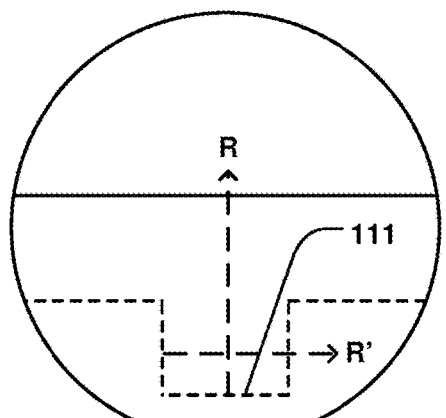
Figure 4D:
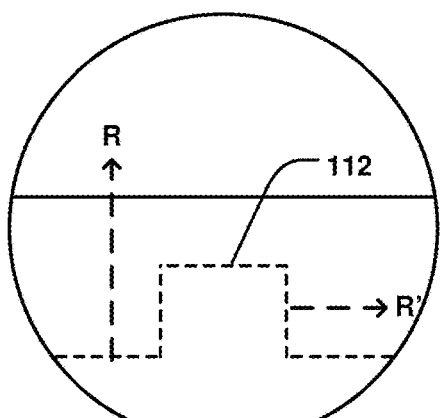
Figure 4E:
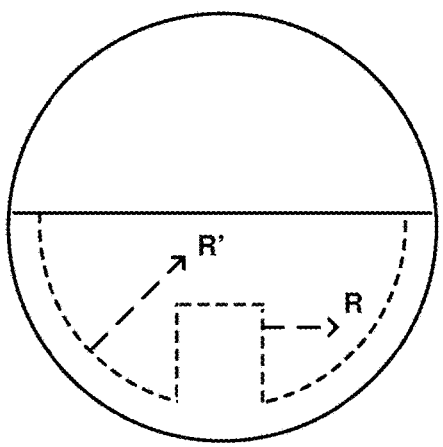
Figure 4F:
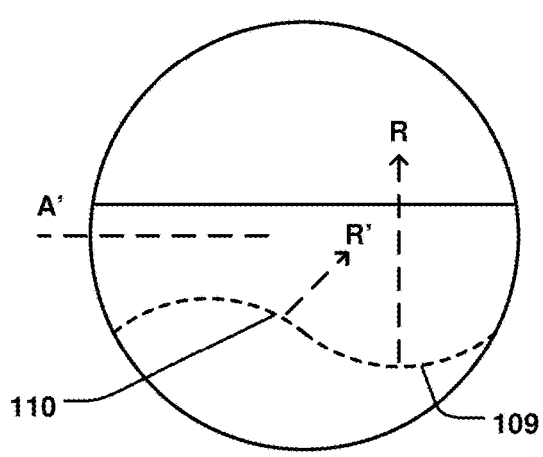
Figure 5:
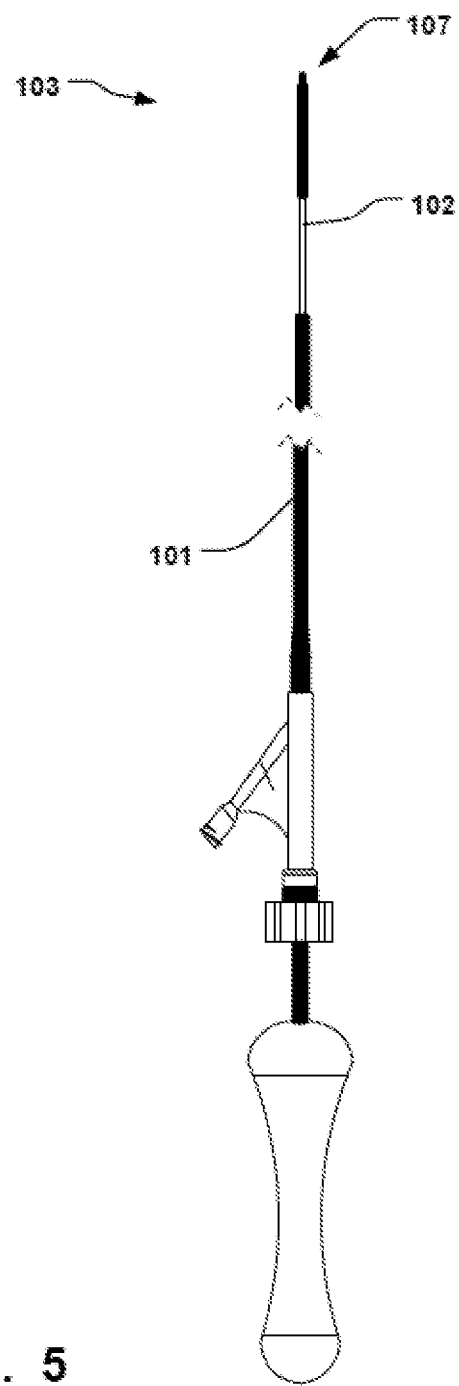
FIG. 5 is an illustration of a medical device according to an embodiment of the invention.

The first or second locking surface may be curved in the radial direction, e.g. as illustrated in FIG. 4f. This provides for a centering ability in order to guide the implant to the correct co-axial position with the wire. Prior art devices have several sharp protrusions that are difficult to navigate to. Further, as mentioned above, since the curved locking surface is advantageously arranged to receive the entire portion of the implant that is in contact with the distal wire 102 in the final locked position, such protrusions are not required for the present device according to the invention, due to the entire receiving surface contributing to the guiding, i.e. the radius of curvature—e.g. in the radial direction—of the locking surface of the present invention is much larger than that of the prior art devices having sharp protrusions each with small radius of curvature, and therefore the present invention can accommodate a much larger off-set in relation to the final locked position—when making the initial contact to the implant with the wire—and still be able to guide the implant to the correct position.

FIG. 4f illustrates a locking surface that has a sinusoidal shape, however it may also be possible to have any concave or convex shape, or a combination thereof. The implant 200 will in this example have a corresponding complementary curved shape. The surface of the curved portion has a normal direction (perpendicular to the tangent of the curve) that points in varying radial directions. For example, a first radial direction (R) that is directed in the vertical plane is indicated in FIG. 4f at a first point, at the center of the upwardly concave portion of the sinusoidal shape. The curved surface will stop rotational movement since it extends in a radially transverse direction, i.e. with a varying radial distance to the longitudinal axis 105, that will lock rotational movement of an implant 200 having a corresponding surface. Simultaneously, the curved shape will also stop the implant 200 from sliding in a longitudinally transverse direction such as along a direction A' indicated in FIG. 4f since the curved surface also has a normal in a second radial direction (R'), different from the first radial direction (R) that will mate with the corresponding surface of the implant 200 and thereby prevent such transversal movement. This may provide for easier connection to the implant 200 since the curved surface can stop both rotation and transverse/radial movement.

As shown in e.g. FIG. 4f the first locking surface 109 may be continuous with the second locking surface 110. The implant 200 can be easier to capture and retrieve if there is a smooth path for the implant to follow when being positioned in the interlocked state. A continuous locking surface may lock in several directions while allowing an implant to slide into position. The first and second locking surfaces 109, 110, may be overlapping in the longitudinal direction 105. This provides for a simplified locking structure 108 that may be easier to use and manufacture. The first and second locking surfaces 109, 110 may thus be provided as a single surface, such as shown in e.g. FIG. 4f.

The first and second locking surfaces 109, 110, may also be displaced a distance (D) in relation to each other in the longitudinal direction 105, as shown in FIG. 1. This may provide for better stability in the longitudinal direction 105 since the implant 200 is locked at each locking surface 109, 110, along the longitudinal direction 105. It may thus require a larger force to accidentally angle the implant relative the longitudinal direction 105.

The second locking surface 110 may be a recess 111 in the first locking surface 109, such as shown in FIG. 4c. The recess 111 will have a surface facing a second radial direction (R') different from a first radial direction (R). Accordingly, the recess 111 will be effective in stopping rotational movement and also movement transverse to the longitudinal direction 105, when interlocking with a corresponding mating surface of the implant 200, i.e. a protrusion. Alternatively or in addition the second locking surface 110 may also be protrusion 112 in the first locking surface 109, as shown in FIG. 4d or 4e. In FIG. 4e, the second locking surface 110 is illustrated as a partly cylindrical surface, that will stop the implant from moving in a transverse, e.g. radial direction relative longitudinal axis 105, i.e. to the left and right in the figure in the horizontal plane. It should be noted that movement in the vertical plane is hindered in the downward direction by the first and/or second locking surface 109,110, and movement in the upward direction in the FIGS. 4a-f is stopped by the sheath 101 when the locking structure 107 is withdrawn into the sheath 101. Returning to FIG. 4e, the protrusion having a vertical surface facing the first radial direction (R) will prevent rotational movement of the implant 200.

Figure 6A:
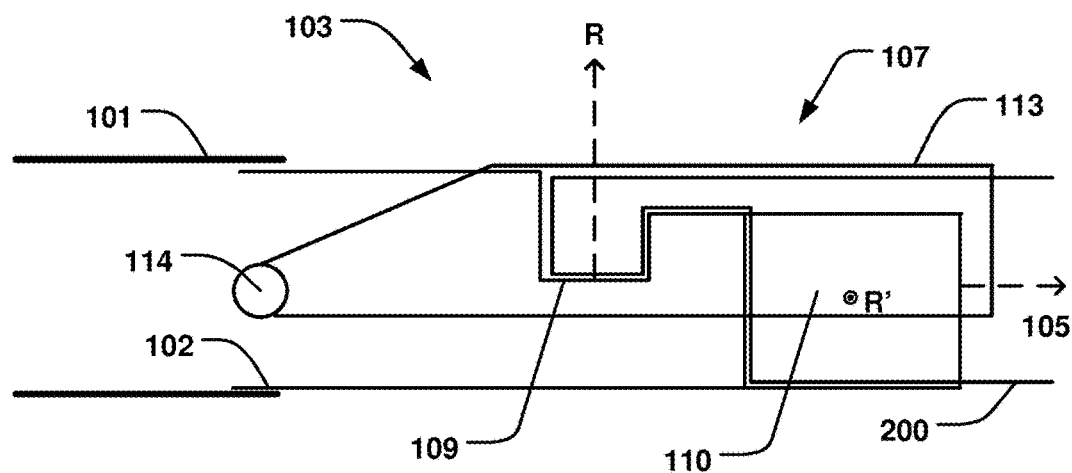
FIGS. 6a-b are illustrations of a medical device and implant according to embodiments of the invention.
Figure 6B:
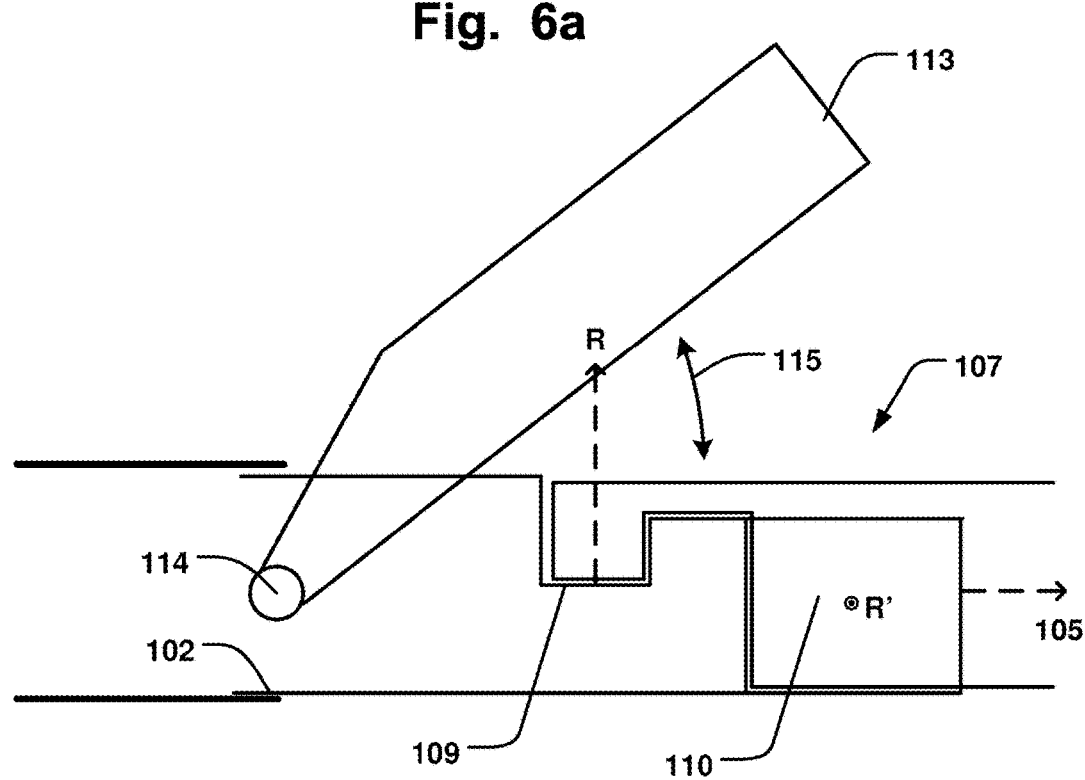
Figure 7A:
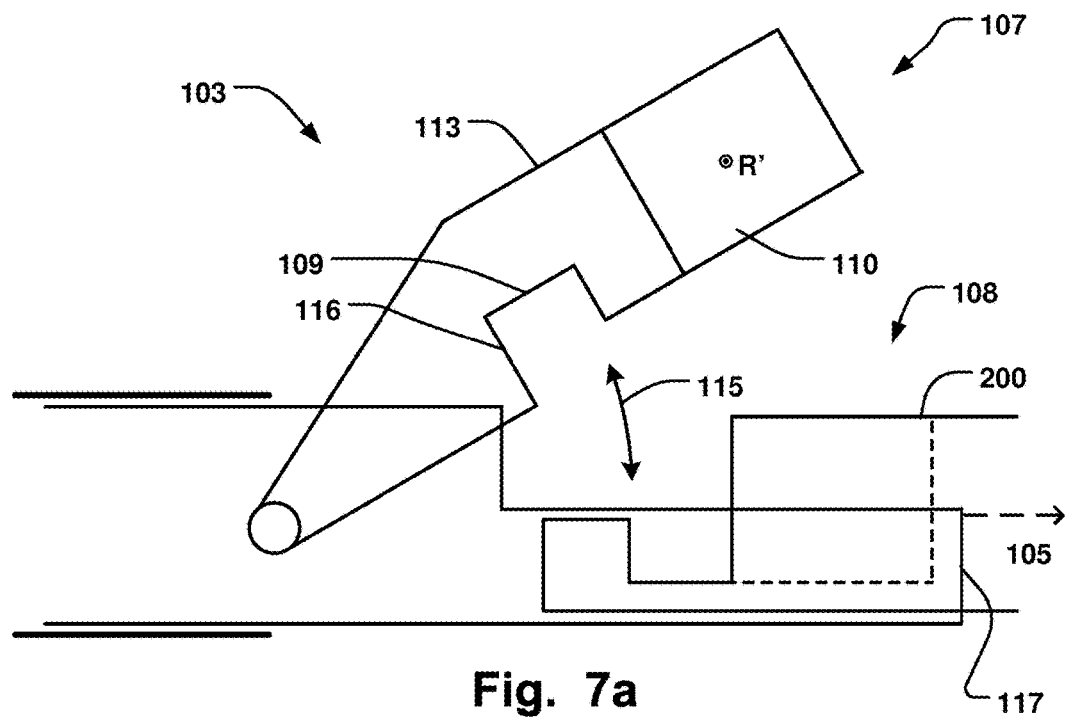
FIGS. 7a-b are illustrations of a medical device and implant according to embodiments of the invention.
Figure 7B:
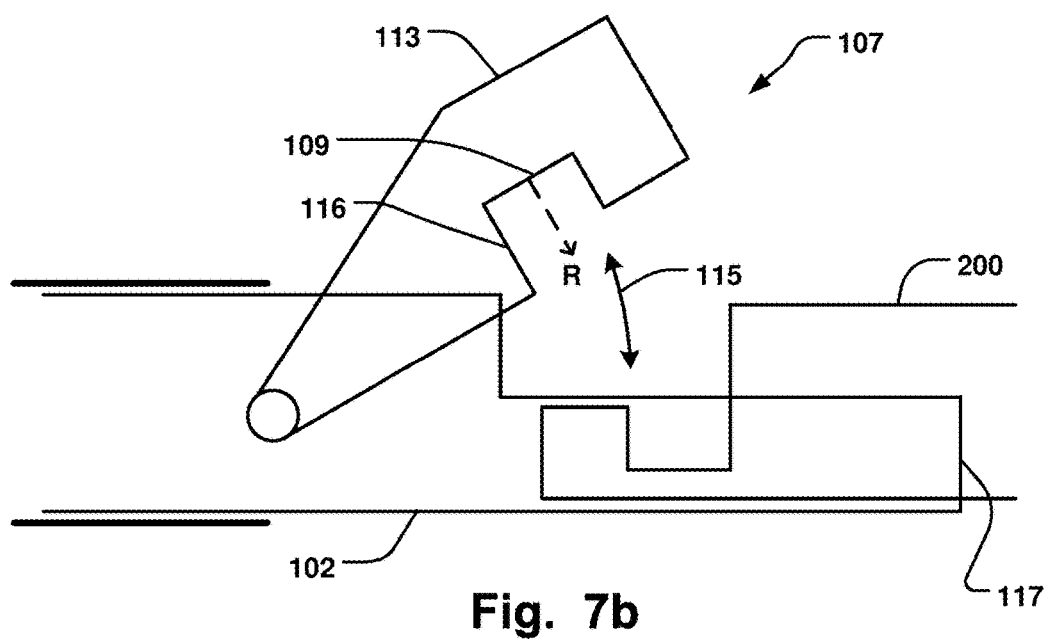

The wire 102 may comprise a pivotable locking portion 113 having a closed and an open position, such as illustrated in FIGS. 6a and 6b respectively. The closed position of the pivotable locking portion 113 locks movement of the implant 200, when received in the locking structure 107, in a radial direction. The radial direction may be the first radial direction (R) as illustrated in FIGS. 6a-b. Since the first locking surface 109 faces the first radial direction (R), it may be desirable to fixate the position of the implant 200 in the direction of the normal to the first locking surface 109. This allows the implant 200 to be fixated in all direction without having to retract the locking structure 107 inside the sheath 101. Further, the pivotable locking portion 113 may grab the implant 200 if it's going to be retrieved. This may facilitate engagement of the implant and locking the implant 200 into the correct position before retracting the implant inside the sheath 101, or to get a stable hold of the implant before it is repositioned at the target site. The pivotable locking portion 113 may also be arranged to lock the position in the second radial direction (R') or in any other radial direction. The pivotable locking portion 113 may be mounted to rotate around a pivoting axis 114 at the wire 102, and may be engaged with a separate locking wire (not shown) to be moved between the closed and the open position with an angle 115. FIGS. 7a-b shows an alternative configuration where the locking portion 113 has a locking structure 107 with a recess 116 with a first locking surface 109, and also a second locking surface 110, that engages with a complementary mating surface 108 of the implant 200. Hence, instead of having the locking surface 107 at the distal end of the wire, it may be provided at the pivotable locking portion 113. The distal end of the wire 102 that receives the implant 200 may have a recess, such as a partly cylindrical portion 117, that receives a corresponding cylindrical portion of the implant 200. This may allow the implant 200 to easily engage with the wire before locked into position by the pivotable locking portion 113. The cylindrical portion 117 extends in the longitudinal direction 105, and it may be shaped to conform to a corresponding complementary shaped portion of the implant 200. This provides for a secure fit between the cylindrical portion 117 and the implant, so while the implant may slide easily into the cylindrical portion it is also provided for a secure positioning of the implant on the distal end of the wire 102. E.g. dislocation of the implant in the radial directions are prevented by the side walls of the cylindrical portion. Such side walls are also illustrated in FIG. 4e. Stabilization and positioning of the implant at the distal end of the wire is achieved even if excluding the rectangular element in FIG. 4e. Having only smooth concave side walls, such as a partly tubular portion, at the distal end, may facilitate the capturing of the implant with the wire 102 since the implant may glide smoothly into position. Prior art devices has complicated interlocking patterns that makes such coupling more difficult. When the implant has slided into position, the wire 102 may either be withdrawn for securement into the sheath, and/or a pivoting locking portion 113 may close over the distal end to fixate the implant. The advantageous effects provided by having concave surfaces at the distal end of the wire 102 are thus provided for both types of interlocking mechanism, i.e. for withdrawal into the sheath as seen in e.g. FIG. 3b, and for the pivoting locking portion as seen in e.g. 7b. Such concave portion is illustrated also in FIG. 4f, see locking surface 109, where non-concentrical positioning of the surface 109 in relation to the symmetrical (rotational) axis in the cross-section view of the wire 102 is shown. I.e. the rotational axis extends in the longitudinal direction. Such non-concentrical arrangement provides for locking of rotational movement of the implant while maintaining the ease of implant capture since it can glide smoothly into position due to the concave or partly circular surface 109. As further seen in FIG. 4f, the distal end of the wire may also have a partly circular surface such as a convex portion, see locking surface 110, which allows smooth guiding of the implant into the correct position. In the example in FIG. 4f, the convex surface 110 and concave surface 109 are in continuous connection with each other, e.g. a sinusoidal shape as described above. As mentioned, prior art devices has complicated interlocking patterns that does not allow such smooth guiding of the implant into the correct position at the wire 102. When having a pivotable locking portion 113 it is not necessary to have non-concentrical concave or convex surface, since the locking portion 113 may have a locking structure 107 that stops rotational movement of the implant. The locking structure 107 can also stop longitudinal movement by having e.g. a recess 116.

FIG. 7b shows an arrangement where the second locking surface 110 has been omitted. The first locking surface 109 of the pivotable locking portion mates with the implant 200 to fixate the position in the longitudinal direction 105, and to stop rotational movement of the implant. Thus the locking structure 107 comprises a recess 116, having the first locking surface 109 which interlocks with the implant 200. Thus the implant 200 can be fixated without having to interlock with a locking structure of the wire 102, since the locking structure is provided in the pivoting locking portion 113. This allows for maintaining a small profile or cross-section of the delivery device since the wire 102 itself does not need a locking structure, and the implant can thereby be align co-axially with the wire 102 in the initial approach, e.g. during a retrieval procedure. Prior art devices requires the implant to be lifted—i.e. moved in the radial direction—for positioning into the interlocking structure of the wire 102. The surrounding anatomy may not allow such movement. The pivoting locking portion 113 may be moved only slightly in the radial direction and still interlock with the implant with the recess 116. Having the recess 116 in the pivoting locking portion also allows for more easy advancement of the implant into the final locked position, since the pivoting portion exerts a force moving towards the closed position that pushes the recess 116 over the implant 200. The wire 102 may have a recess, such as a partly cylindrical portion 117, which simultaneously hinders movement of the implant in a direction transverse to the longitudinal direction 105, e.g. in a direction perpendicular to the longitudinal direction and the first radial direction (R). This may allow easy fixation of the implant while maintaining stability.

The locking surface 109 may be curved in a radial direction. This allows the implant 200 to slide into the correct co-axial position with the wire 102, i.e. centering is achieved, without the requirement of having other locking surfaces of the wire in order to achieve centering.

The medical implant delivery and retrieval device 100 may comprise a retrieval element 118 (now shown) connecting the locking structure 107 and the implant 200 when the implant is disconnected from the locking structure 107. The retrieval element 118 may hence serve as a security wire that can be engaged to retract the implant towards the locking structure 107 if desired. This may allow for easier navigation of the implant 200 towards the locking structure 107 and improving the security of the procedure.

Alternatively or in addition, the locking structure 107 may comprise an element 119 (not shown) for attracting the implant 200 with a force, such as a magnet. Also, the magnet force may be switchable to an off state that may ease detachment of the implant 200 from the locking structure. The implant may also be pushed away from the magnet with a pusher (not shown) that is movable within a lumen of the locking structure 107 and exiting and extending beyond a distal end thereof, in order to again disengage the implant 200 after being captured with the magnet. Insertion of such pusher in the locking structure may disengage the first and/or second locking surfaces from the implant 200.

Figure 8A:
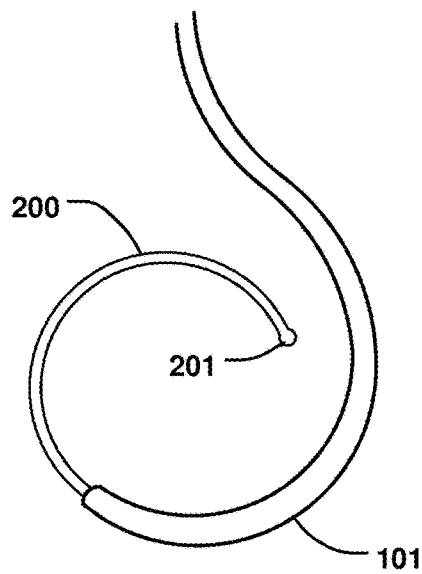
FIG. 8 are illustrations of a medical device and implant according to embodiments of the invention.
Figure 8B:
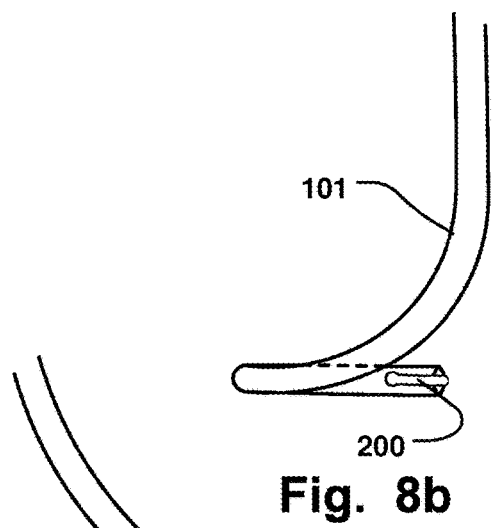
Figure 8C:
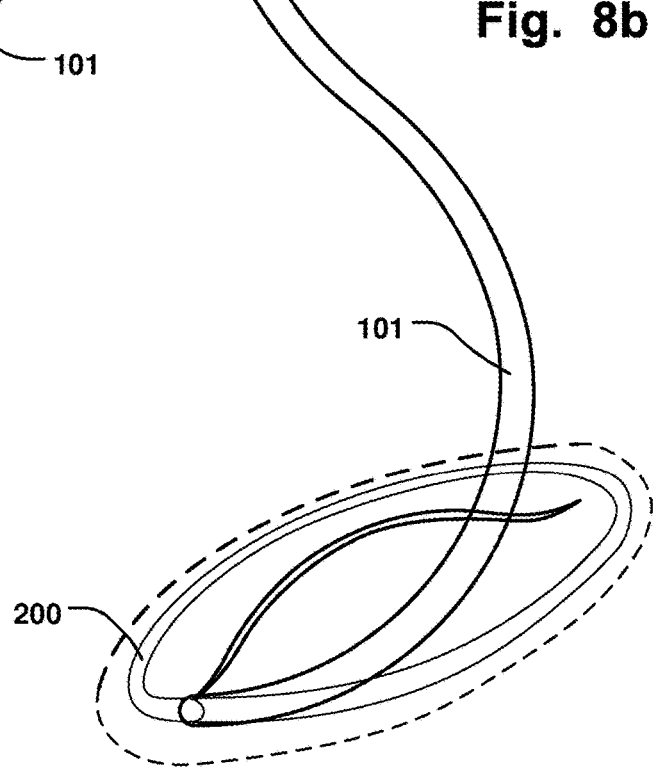

FIGS. 8a-c illustrates a sheath 101 that is steerable or shaped to allow for an improved delivery and/or retrieval angle of the implant 200, so that it can be more easily and accurately positioned. The sheath 101 may have a delivery configuration where it extends along a 3-dimensional path to position its distal end at a defined angle. Thus, the sheath 101 may assume a desired curve shape to optimize the positioning of the implant such as an annuloplasty ring or helix. FIG. 8a show a partly circular configuration of the sheath in a top-down view, and FIG. 8b show a side view of the sheath 101. The resulting angle from which the implant 200 can be delivered is flat and close to parallel with respect to the valve, which allows for accurate positioning and easy insertion of the implant 200 when it exits the sheath 101. The implant 200 may be shaped from a flexible alloy such as Nitinol, and it is pre-shaped by heat treatment to assume a desired shape when exiting the sheath or catheter 101. In addition the implant 200 may comprise an atraumatic tip at its distal end, such as a partly spherical portion, to avoid damaging the tissue.

A kit is disclosed according to one embodiment comprising a medical implant delivery and retrieval device 100, and an annuloplasty implant 200 such as an annuloplasty ring or helix, wherein the annuloplasty implant 200 comprises the complementary mating surface 108 at an end portion thereof for interlocking with the locking structure 107 the medical implant delivery and retrieval device 100.

An annuloplasty implant 200 is disclosed according to one embodiment, see FIGS. 2a-b, such as an annuloplasty ring or helix comprising complementary mating surface 108 at an end portion thereof for interlocking with a locking structure 107 of a medical implant delivery and retrieval device 100 extending along a longitudinal direction 105. The mating surface 108 comprises a first locking surface 209 aligned in a first radial direction (R) to lock rotational movement of the implant 200, when received in the locking structure 107, around the longitudinal direction 105. The mating surface 108 comprises a recess 216 for locking movement of the implant, when received in the locking structure, in the longitudinal direction 105. This effectively provides control of the implant 200 when received and interlocked with the delivery device 100. Prior art implants suffer from less control and less secure fixation in the delivery device. The recessed surface 216 may comprise the first locking surface 209.

The mating surface 108 may also comprise a second locking surface 210 aligned to face a second radial direction (R'), different from the first radial direction (R), to lock movement of the implant 200, when received in the locking structure 107, transverse to the longitudinal direction 105. Thus, even when not interlocked with the delivery device 100, e.g. by withdrawing the implant inito the sheath 101 or closing the pivoting locking portion 113, such second locking surface will stop movement transverse to the longitudinal direction, e.g. in the radial direction. The recessed surface 216 may comprise the second locking surface 210. Thus locking in the rotational, longitudinal, and radial directions is provided by having such mating surface 108, e.g. a recess 216 as described. Prior art implant provides less secure fixation in all these directions, or have more complex structures that are difficult to manufacture. The complementary mating surface 108 may be shaped to mirror any shape such as described above for the locking portion 107 of the device 100.

The first or second locking surface may be curved in a radial direction. This provides for the advantageous effects described above where the implant may be guided into the correct position in the wire—having the complementary curved surface—by a sliding motion along the curved surface. This allows easier capturing and fixation of the implant 200.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical implant delivery and retrieval device comprising
a sheath,
a wire having a distal end and being movable in a lumen of said sheath in a longitudinal direction of said sheath, said distal end comprising a locking structure for receiving and interlocking with a complementary mating surface of a medical implant,
wherein said locking structure comprises a first locking surface aligned in a first radial direction (R) to lock rotational movement of said implant, when received in said locking structure, around said longitudinal direction,
wherein said wire comprises a pivotable locking portion having an open and a closed position, and the locking portion has a locking structure with a recess locking movement of said implant, when received in said locking structure, in said longitudinal direction, when said locking portion is in the closed position and
wherein said first locking surface is curved in a radial direction.

2. The medical implant delivery and retrieval device according to claim 1, wherein the distal end of the wire that receives the implant has a partly cylindrical portion.

3. The medical implant delivery and retrieval device according to claim 1, wherein said locking structure comprises a second locking surface aligned to face a second radial direction (R'), different from said first radial direction, to lock movement of said implant, when received in said locking structure, transverse to said longitudinal direction.

4. The medical implant delivery and retrieval device according to claim 3, wherein said second locking surface is curved in a radial direction.

5. The medical implant delivery and retrieval device according to claim 4, wherein said first locking surface is concave or convex.

6. The medical implant delivery and retrieval device according to claim 4, wherein said second locking surface is concave or convex.

7. The medical implant delivery and retrieval device according to claim 4, wherein said first locking surface is positioned non-concentrically with respect to a symmetrical rotational axis of the wire extending in the longitudinal direction.

8. The medical implant delivery and retrieval device according to claim 4, wherein said second locking surface is positioned non-concentrically with respect to a symmetrical rotational axis of the wire extending in the longitudinal direction.

9. The medical implant delivery and retrieval device according to claim 3, wherein said first and second locking surfaces are displaced a distance (D) in relation to each other in said longitudinal direction.

10. The medical implant delivery and retrieval device according to claim 3, wherein said first and second locking surfaces are overlapping in said longitudinal direction.

11. The medical implant delivery and retrieval device according to claim 10, wherein said first locking surface is continuous with said second locking surface.

12. The medical implant delivery and retrieval device according to claim 3, wherein said second locking surface is a recess or protrusion in said first locking surface.

13. The medical implant delivery and retrieval device according to claim 1, wherein said locking structure is open radially outwards to receive said complementary mating surface in a radial direction.

14. The medical implant delivery and retrieval device according to claim 1, wherein said first locking surface has a sinusoidal shape.

15. The medical implant delivery and retrieval device according to claim 1, wherein said locking structure is arranged to receive said complementary surface when said locking structure extends outside said sheath, and to interlock with said complementary surface and fixate the position of said implant relative said locking structure when said locking structure is retracted within said sheath.

16. The medical implant delivery and retrieval device according to claim 1, comprising a retrieval element connecting said locking structure and said implant when said implant is not received in said locking structure.

17. The medical implant delivery and retrieval device according to claim 1, wherein said locking structure comprises an element for attracting said implant with a magnet.

18. The medical implant delivery and retrieval device according to claim 1, wherein said sheath is steerable, and/or wherein said sheath has a delivery configuration where said sheath extends along a 3-dimensional path to position said distal end at a defined angle.

19. The medical implant delivery and retrieval device according to claim 1, wherein said device is adapted for delivering and retrieving a cardiac valve implant.

20. A kit comprising a medical implant delivery and retrieval device according to claim 1, and an annuloplasty implant, wherein said annuloplasty implant comprises said complementary mating surface-at an end portion thereof for interlocking with said locking structure of the medical implant delivery and retrieval device.

21. A medical implant delivery and retrieval device comprising
a sheath,
a wire having a distal end and being movable in a lumen of said sheath in a longitudinal direction of said sheath, said distal end comprising a locking structure for receiving and interlocking with a complementary mating surface of a medical implant,
wherein said locking structure comprises a locking surface-aligned in a radial direction (R, R') to lock rotational movement of said implant, when received in said locking structure, transverse to said longitudinal direction,
wherein said locking surface is curved in a radial direction.

22. The medical implant delivery and retrieval device according to claim 21, wherein said locking surface is concave or convex.

23. The medical implant delivery and retrieval device according to claim 21, wherein said locking surface is positioned non-concentrically with respect to a symmetrical rotational axis of the wire extending in the longitudinal direction.

24. An annuloplasty implant comprising a complementary mating surface at an end portion thereof for interlocking with a locking structure of a medical implant delivery and retrieval device extending along a longitudinal direction,
wherein said complementary mating surface comprises a first locking surface aligned in a first radial direction (R) to lock rotational movement of said implant, when received in said locking structure, around said longitudinal direction, and a recess for locking movement of said implant, when received in said locking structure, in said longitudinal direction and wherein said first locking surface is curved in a radial direction.

25. The annuloplasty implant according to claim 24, wherein said mating surface comprises a second locking surface aligned to face a second radial direction (R'), different from said first radial direction, to lock movement of said implant, when received in said locking structure, transverse to said longitudinal direction.

26. The annuloplasty implant-according to claim 24, wherein said first or second locking surface has a sinusoidal shape.

\* \* \* \* \*